United States Patent [19]
Inomata et al.

[11] Patent Number: 6,011,069
[45] Date of Patent: Jan. 4, 2000

[54] MULTIDRUG RESISTANCE INHIBITORS

[75] Inventors: Kohei Inomata; Toshihiro Takahashi; Hitoshi Inoue; Makoto Yanai; Hiroyuki Yamazaki; Masashi Suzuki; Tsutomu Takasawa; Kouji Kawamura; Norio Oshida; Hiroyuki Ikemoto; Takao Kishiye, all of Saitama-ken, Japan

[73] Assignee: Nisshin Flour Milling Co., Ltd., Tokyo, Japan

[21] Appl. No.: 08/767,624

[22] Filed: Dec. 17, 1996

[30] Foreign Application Priority Data

Dec. 26, 1995 [JP] Japan .................................. 7-339161

[51] Int. Cl.⁷ .................................................. A01N 33/02
[52] U.S. Cl. ........................................... 514/655; 514/649
[58] Field of Search ............................................. 514/655

[56] References Cited

U.S. PATENT DOCUMENTS

| | | | |
|---|---|---|---|
| 4,645,862 | 2/1987 | Tahara et al. | 564/370 |
| 4,658,063 | 4/1987 | Tahara et al. | 564/367 |
| 4,700,002 | 10/1987 | Tahara et al. | 564/367 |
| 4,723,008 | 2/1988 | Tahara et al. | 544/401 |

FOREIGN PATENT DOCUMENTS

| | | |
|---|---|---|
| WO 94/10995 | 5/1994 | France . |
| 1-36457 | 7/1989 | Japan . |
| 0 355 604 | 2/1990 | Japan . |
| 2-138211 | 5/1990 | Japan . |
| 3-2150 | 1/1991 | Japan . |
| 5-16411 | 3/1993 | Japan . |
| 2099424 | 12/1982 | United Kingdom . |

OTHER PUBLICATIONS

Patent Abstracts of Japan, vol. 11, No. 30, (C–400), Jan. 29, 1987, JP 61 200913, Sep. 5, 1986.

Journal National Cancer Institute, vol. 76, No. 5, pp. 947–953, May 1986, Teruhito Yamaguchi, et al., "Overcoming Drug Resistance in Cancer Cells with Synthetic Isoprenoids".

Takashi Tsuruo, et al. "Overcoming of Vincristine Resistance in P388 Leukemia in Vivo and in Vitro through Enhanced Cytotoxicity of Vincristine and Vinblastine by Verapamil", Cancer Research, vol. 41, (pp. 1967–1972), May 1981.

Carol O. Cardarelli, et al. "Differential Effects of P–Glycoprotein Inhibitors on NIH3T3 Cells Transfected with Wild–ype (G185) or Mutant (V185) Multidrug Transporters", Cancer Research, vol. 55, (pp. 1086–1091), Mar. 1, 1995.

*Primary Examiner*—Dwayne C. Jones
*Attorney, Agent, or Firm*—Oblon, Spivak, McClelland, Maier & Neustadt, P.C.

[57] ABSTRACT

There is disclosed a multidrug resistance inhibitor for overcoming a multidrug resistance of cancer, or an agent for enhancing the activity of anti-cancer agents, which comprises as an active ingredient a compound of formula (I) or a pharmaceutically acceptable salt thereof:

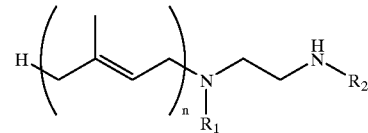

(I)

wherein
n is an integer of 5 to 12,
$R_1$ and $R_2$ are each independently benzyl, of which a phenyl ring may be substituted by 1 to 5 substituents selected from hydroxy, $(C_1-C_4)$alkyl, $(C_1-C_4)$alkoxy and halogen, and/or by methylenedioxy, with the proviso that $R_1$ and $R_2$ are simultaneously not a compound of formula (II)

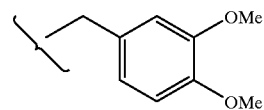

(II)

3 Claims, No Drawings

MULTIDRUG RESISTANCE INHIBITORS

FIELD OF THE INVENTION

This invention relates to multidrug resistance inhibitors for overcoming multidrug resistance of cancer which is found in cancer chemotherapy, and also agents for enhancing the activity of anti-cancer agents.

BACKGROUND OF THE INVENTION

It is a common problem for human beings to overcome cancer. For the purpose, many anti-cancer agents have been developed until now, but the expression of multidrug resistance of cancer has become a clinical problem. Multidrug resistance is a phenomenon (cross-resistance) in which cancer cells resist to not only the particular anti-cancer agent administered, but also the other anti-cancer agents, due to an administration of an anti-cancer agent or a resistance of cancer cells by nature to anti-cancer agents. Reportedly, about 50% of patients newly diagnosed as cancer showed a drug resistance in the treatment of cancer, and more than 90% of the deaths showed some behaviors associated with the resistance of cancer cells to anti-cancer agents during the treatment with anti-cancer agents. Therefore, it has become extremely important in cancer chemotherapy to overcome multidrug resistance to anti-cancer agents of cancer cells.

Although a mechanism of cancer cells causing multidrug resistance has not been clearly elucidated, it is considered to result from a reduced concentration of anti-cancer agents in the cells when said cells have acquired multidrug resistance. On the other hand, many cancer cells having multidrug resistance produce P-glycoprotein excessively and this P-glycoprotein may play a role in transporting anti-cancer agents out of the cells. P-glycoprotein is coded by a gene called MDR1 on human being. Thus the over-expression of MDRI gene in human cancer cells is considered to be a cause of acquiring resistance (MDR1 resistance). P-glycoprotein has low substrate specificity and can bind with various kinds of compounds to transport drugs out of the cells. It follows that once P-glycoprotein expresses in cancer cells, the cells will acquire resistance to many other anti-cancer agents. In fact, it is known that many structurally different anti-cancer agents such as adriamycin, vinblastine, vincristine, actinomycin D, colchicine become a substrate for transporting outside cells by P-glycoprotein. Therefore, it is considered that inhibiting the function of P-glycoprotein will lead to overcoming multidrug resistance. It is reported that about 30% of multidrug resistances is caused by P-glycoprotein.

It is known that messenger RNA of MDR1 gene encoding P-glycoprotein expresses in normal tissue, for example, kidney, adrenal, large intestine, small intestine, intestinum colon, lung, liver, pancreas, or lymphocyte. In kidney P-glycoprotein plays a part to transport drugs out of the body. The reason why anti-cancer agents have low activity in kidney cancer where kidney cells were cancerous is that P-glycoprotein produced therein will transport anti-cancer agents outside the cells. Recently, it is found that the main substance of blood brain barrier which controls transport of drugs into the brain is P-glycoprotein. This means that the concentration of anti-cancer agents delivered into brain, kidney, adrenal, large intestine, small intestine, intestinum colon, lung, liver, pancreas, lymphocyte of leukemia, etc., can be increased by inhibiting P-glycoprotein. Thus, P-glycoprotein inhibitors are expected to enhance effect of anti-cancer agents on brain tumor, kidney cancer, adrenal cancer, large intestine cancer, small intestine cancer, intestinum colon cancer, lung cancer, liver cancer, pancreas cancer, or leukemia, etc.

In the field of cancer chemotherapy, many anti-cancer agents have been used such as mitomycin, cyclophosphamide, melphalan, nimustine, carboquone, vincristine, vinblastine, vindesine, bleomycin, 5-fluorouracil, adriamycin, cisplatin, actinomycin D, methotrexate, aclarubicin, toyomycin, neocarzinostatin, ifosfamide, etoposide, camptothecin, doxorubicin, irinotecan. Those drugs have characteristic anti-cancer spectra. Some of those anti-cancer agents are known to bring about a resistance of cancer cells to the agents by continuous or a long term administration. Further, the problem of cross-resistance has arisen. Therefore it has been required to activate or enhance the sensitivity of cancer cells having resistance to anti-cancer agents in the field of cancer chemotherapy.

Taxol and its derivative taxotere were approved in U.S.A. in recent years, and will be done in Japan. They are expected to be one of the leading drugs of solid carcinoma chemotherapy in the future, because of having a potent and strong anti-cancer activity, particularly in the field of solid carcinoma. However, taxol is known to be a substrate for transporting outside cells by P-glycoprotein, and its activity may be weakened by MDR1 resistance. Recently, it is reported that P-glycoprotein inhibitors can overcome taxol resistance in MDR1 resistance cells (Cancer Res. vol. 55, 1086–1091, 1995). This shows that P-glycoprotein inhibitors are also effective for taxol resistance.

Some of the instant compounds are included in a series of isoprenylamine derivatives having anti-viral and anti-tumor activities disclosed in Japanese Patent Kokoku 1-36457 in which there is no reference that the isoprenylamine derivatives have the function as multidrug resistance inhibitors for overcoming multidrug resistance of cancer.

Tsuruo et al. report that verapamil represented by the following formula (III)

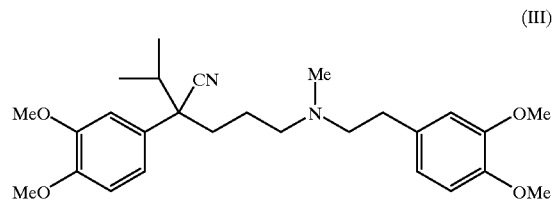

(III)

inhibits P-glycoprotein and overcomes MDR1 resistance (Cancer Res., vol. 41, 1967–1972, 1981).

Nakagawa et al., Japanese Patent Kokoku 5-16411 discloses a compound of formula (IV)

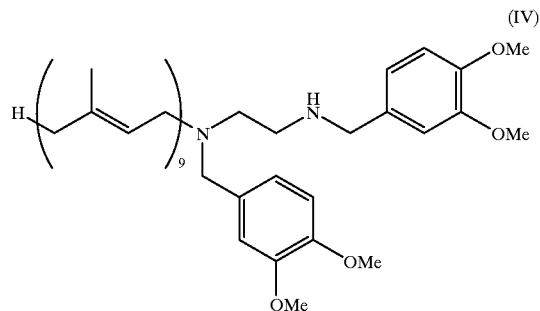

(IV)

and the pharmaceutically acceptable salts thereof, which have an activity of overcoming adriamycin (ADM) resistance to ADM, one of anti-cancer drugs. Ogawa et al, Japanese Patent Kokai 2-138211, discloses that the malate of formula (IV) has an activity of enhancing the anti-cancer activity.

There is no report that the compound of formula (IV) enhances an anti-cancer activity of taxol in MDR1 resistance cells.

DETAILED DESCRIPTION OF THE INVENTION

We have studied many compounds for enhancing the activity of anti-cancer agents in an effort to overcome the above-mentioned problems of multidrug resistance of cancer cells. As a result, we have found that the compounds of formula (I) have an activity of overcoming multidrug resistance in MDR1 resistance cells, without $Ca^{2+}$ antagonist activity and with a low cytotoxicity, and also an activity of enhancing the activity of anti-cancer agents, in particular taxol and its derivatives.

Accordingly, the present invention provides a pharmaceutical composition which comprises as an active ingredient a compound of formula (I), or a pharmaceutically acceptable salt thereof:

(I)

wherein
n is an integer of 5 to 12,
$R_1$ and $R_2$ are each independently benzyl, of which a phenyl ring may be substituted by 1 to 5 substituents selected from hydroxy, $(C_1-C_4)$alkyl, $(C1-C_4)$alkoxy, and halogen, and/or by methylenedioxy, with the proviso that $R_1$ and $R_2$ are simultaneously not a compound of formula (II)

(II)

The present invention also provides a multidrug resistance inhibitor comprising as an active ingredient a compound of formula (I) or a pharmaceutically acceptable salt thereof. Further, the invention provides an agent for enhancing the activity of anti-cancer agents in the treatment of cancers which include brain tumor, kidney cancer, adrenal cancer, large intestine cancer, small intestine cancer, intestinum colon cancer, lung cancer, liver cancer, pancreas cancer and leukemia. The present invention further provides an agent for enhancing the activity of taxol or its derivatives, which comprises a compound of formula (I) or a pharmaceutically acceptable salt thereof in combination with taxol and its derivatives. The taxol derivatives include, for example, taxotere.

In the compounds of formula (I), the $C_1-C_4$ alkyl group can be straight-chain or branched, which can include methyl, ethyl, n-propyl, isopropyl, n-butyl, sec-butyl, and tert-butyl. The $C_1-C_4$ alkoxy group, the alkyl moiety of which can be straight-chain or branched, can include methoxy, ethoxy, n-propoxy, isopropoxy, n-butoxy, sec-butoxy, tert-butoxy. Halogen can include fluorine, chlorine, bromine and iodine.

Examples of the groups represented by the following formula

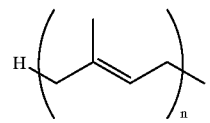

wherein n is an integer of 5 to 12, can include geranylfarnesyl, farnesylfarnesyl, farnesylgeranylgeranyl, farnesylfarnesylgeranyl, solanesyl, decaprenyl, undecaprenyl and dodecaprenyl.

The compounds of formula (I) may be converted, if desired, to the corresponding acid addition salts with pharmaceutically acceptable acids. The acid addition salts are included within the scope of this invention, which can include the salts with inorganic acids such as hydrochloric acid, hydrobromic acid, sulfuric acid, nitric acid and the like, and the salts with organic acids such as fumaric acid, citric acid, maleic acid, phthalic acid, malic acid, tartaric acid or the like.

The compounds of formula (I) can be present in various geometrical isomeric forms, for example, cis/trans isomers. In addition to those compounds of formula (I), possible metabolites induced from the compounds of formula (I) and the metabolic precursors, i.e., "prodrug" which is metabolized in vivo to form the compounds of formula (I), are included within the scope of the present invention.

The compounds of formula (I) may be prepared by various conventional methods, for example, as shown by the following Route 1 or 2.

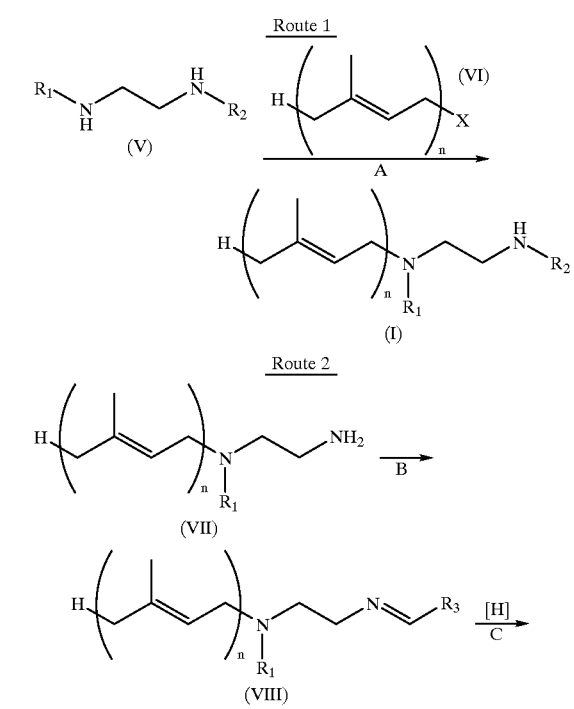

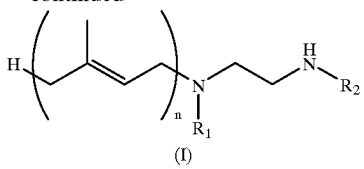

(I)

Route 1 illustrates a process for the preparation of the compounds of formula (I) wherein $R_1$ and $R_2$ are identical, in accordance with the process described in Japanese Patent Kokai 3-2150.

Step A in Route 1 is the step of reacting a compound of formula (V)

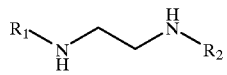

(V)

wherein $R_1$ and $R_2$ are as defined above and both are identical, with a compound of formula (VI)

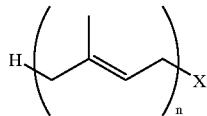

(VI)

wherein n is as defined above, and X is a leaving group such as halogen and sulfonate to prepare the compounds of formula (I) wherein $R_1$ and $R_2$ are identical.

In the above Step A, the reaction is carried out in the presence or absence of solvents using 0.1–10 moles of a compound of formula (VI) per mole of a compound of formula (V). In this reaction, various bases may be added, if necessary, which include carbonates such as potassium carbonate, sodium carbonate, sodium hydrogencarbonate; hydroxides such as sodium hydroxide, potassium hydroxide, lithium hydroxide; amines such as triethylamine, diethylamine, diisopropylethylamine, tributylamine, diisopropylamine, trimethylamine; pyridines such as pyridine, 4-dimethylaminopyridine. Diisopropylamine is preferably used.

The solvents employed in Step A are not specifically limited, unless giving an influence on the reaction, which can include hydrocarbons such as benzene, toluene, xylene, hexane, and heptane; halogenated hydrocarbons such as chloroform, methylene chloride, carbon tetrachloride, and 1,2-dichloroethylene; ethers such as diethyl ether, diisopropyl ether, tetrahydrofuran, and dioxane; amides such as dimethylformamide, dimethylacetamide, and hexamethylphosphoric triamide; alcohols such as methanol, ethanol, and isopropanol; sulfoxides such as dimethylsulfoxide; sulforan; water; and these mixed solvents.

Examples of compounds represented by formula (VI) can include geranylfarnesyl chloride, farnesylfarnesyl chloride, farnesylgeranylgeranyl chloride, farnesylfarnesylgeranyl chloride, solanesyl chloride, decaprenyl chloride, undecaprenyl chloride, dodecaprenyl chloride, geranylfarnesyl bromide, farnesylfarnesyl bromide, farnesylgeranylgeranyl bromide, farnesylfarnesylgeranyl bromide, solanesyl bromide, decaprenyl bromide, undecaprenyl bromide, dodecaprenyl bromide, geranylfarnesyl iodide, farnesylfarnesyl iodide, farnesylgeranylgeranyl iodide, farnesylfarnesylgeranyl iodide, solanesyl iodide, decaprenyl iodide, undecaprenyl iodide, dodecaprenyl iodide, methanesulfonyl geranylfarnesol, methanesulfonyl farnesylfarnesol, methanesulfonyl farnesylgeranylgeraniol, methanesulfonyl farnesylfarnesylgeraniol, methanesulfonyl solanesol, methanesulfonyl decaprenol, methanesulfonyl undecaprenol, methanesulfonyl dodecaprenol, ethanesulfonyl geranylfarnesol, ethanesulfonyl farnesylfarnesol, ethanesulfonyl farnesylgeranylgeraniol, ethanesulfonyl farnesylfarnesylgeraniol, ethanesulfonyl solanesol, ethanesulfonyl decaprenol, ethanesulfonyl undecaprenol, ethanesulfonyl dodecaprenol, propanesulfonyl geranylfarnesol, propanesulfonyl farnesylfarnesol, propanesulfonyl farnesylgeranylgeraniol, propanesulfonyl farnesylfarnesylgeraniol, propanesulfonyl solanesol, propanesulfonyl decaprenol, propanesulfonyl undecaprenol, propanesulfonyl dodecaprenol, butanesulfonyl geranylfarnesol, butanesulfonyl farnesylfarnesol, butanesulfonyl farnesylgeranylgeraniol, butanesulfonyl farnesylfarnesylgeraniol, butanesulfonyl solanesol, butanesulfonyl decaprenol, butanesulfonyl undecaprenol, butanesulfonyl dodecaprenol, isopropylsulfonyl geranylfarnesol, isopropylsulfonyl farnesylfarnesol, isopropylsulfonyl farnesylgeranylgeraniol, isopropylsulfonyl farnesylfarnesylgeraniol, isopropylsulfonyl solanesol, isopropylsulfonyl decaprenol, isopropylsulfonyl undecaprenol, isopropylsulfonyl dodecaprenol, p-toluenesulfonyl geranylfarnesol, p-toluenesulfonyl farnesylfarnesol, p-toluenesulfonyl farnesylgeranylgeraniol, p-toluenesulfonyl farnesylfarnesylgeraniol, p-toluenesulfonyl solanesol, p-toluenesulfonyl decaprenol, p-toluenesulfonyl undecaprenol, and p-toluenesulfonyl dodecaprenol.

The reaction may be carried out at a temperature broadly ranging from ice-cooling to reflux-heating. The reaction time can be varied, depending on a reagent and a reaction temperature, etc., but is usually 0.5 to 36 hours. This reaction is preferably carried out at a temperature of 10 to 30° C. for 1 to 24 hours in the solvent such as ethers. More preferably, this reaction is carried out at a temperature of 10 to 25° C. for 1 to 12 hours in tetrahydrofuran in the presence of diisopropylamine.

Route 2 illustrates a process for the preparation of the compounds of formula (I) wherein $R_1$ and $R_2$ are the same or different.

Step B in Route 2 is the step of reacting a compound of formula (VII)

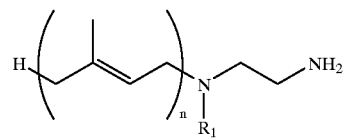

(VII)

wherein n and $R_1$ are as defined above, with a compound of formula (IX)

$R_3CHO$ (IX)

wherein $R_3$ is a phenyl group which may be substituted by 1 to 5 substituents selected from hydroxy, $(C_1-C_4)$alkyl, $(C_1-C_4)$alkoxy, and halogen, and/or by methylenedioxy, in the presence or absence of solvents to prepare a compound of formula (VIII) wherein n, $R_1$ and $R_3$ are as defined above.

This reaction may be carried out while removing a producing water with Dean-Stark apparatus, etc., or in the presence of dehydrating agents such as anhydrous sodium carbonate, anhydrous potassium carbonate, anhydrous sodium sulfate, anhydrous potassium chloride, anhydrous magnesium sulfate and molecular sieve. In general, the reaction is preferably carried out in the presence of a solvent. The solvents employed in this reaction are not specifically limited, unless giving an influence on the reaction, which can include hydrocarbons such as benzene, toluene, xylene, hexane, and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and hexamethylphosphoric triamide; alcohols such as methanol, ethanol and isopropanol; sulfoxides such as dimethylsulfoxide; sulforan; and these mixed solvent.

The reaction may be carried out at a temperature broadly ranging from ice-cooling to reflux-heating. The reaction time can be varied, depending on a reagent and a reaction temperature, etc., but is usually 0.5 to 12 hours. This reaction is preferably carried out at a temperature from ice-cooling to reflux-heating for 1 to 5 hours in the presence of the solvents such as hydrocarbons and alcohols or the mixed solvents of alcohols and halogenated hydrocarbons. More preferably, this reaction is carried out at a temperature ranging from 0° C. to reflux-heating for 0.5 to 3 hours in the presence of methanol or ethanol, or the mixed solvent of methanol and chloroform.

Step C in Route 2 is the step of reducing a compound of formula (VIII) to prepare the compounds of formula (I). This reaction is usually carried out in the presence of a reducing agent. The reducing agents which can be used include metal hydrides such as lithium borohydride, sodium borohydride, sodium cyanoborohydride, lithium aluminium hydride and diisobutyl aluminium hydride. This reaction is usually carried out in the presence of a solvent. The solvents used are not specifically limited, unless giving an influence on the reaction, which can include hydrocarbons such as benzene, toluene, xylene, hexane and heptane; halogenated hydrocarbons such as chloroform, methylene chloride, carbon tetrachloride and 1,2-dichloroethylene; ethers such as diethyl ether, diisopropyl ether, tetrahydrofuran and dioxane; amides such as dimethylformamide, dimethylacetamide and triamide hexamethylphosphate; alcohols such as methanol, ethanol and isopropanol; sulfoxides such as dimethylsulfoxide; water; and these mixed solvents.

The reaction may be carried out at a temperature broadly ranging from ice-cooling to reflux-heating. The reaction time can be varied, depending on a reagent and a reaction temperature, etc., but is usually 0.5 to 24 hours. Preferably, this reaction is carried out at a temperature ranging from ice-cooling to 50° C. for 0.5 to 5 hours in the presence of sodium borohydride or sodium cyanoborohydride in the solvent such as alcohols or the mixed solvents of alcohols and halogenated hydrocarbons.

The reactions in the above Steps B and C may be optionally carried out in the same vessel. More specifically, a compound of formula (VII) and a compound of formula (IX) are reacted in a solvent to give a compound of formula (VIII), followed by reducing the compound of formula (VIII) with a reducing agent in the same vessel to give a compound of formula (I). Preferably, this reaction is carried out by reacting the compounds of formulas (VII) and (IX) at a temperature ranging from 0° C. to reflux-heating in alcohols, in particular methanol or ethanol, or the mixed solvents of alcohols and halogenated hydrocarbons, in particular, those of methanol and chloroform, to afford the compound of formula (VIII), followed by reducing the compound of formula (VIII) in the same vessel with a reducing agent of sodium borohydride or sodium cyanoborohydride at a temperature of 0 to 30° C. for 0.5 to 3 hours.

The invention provides a pharmaceutical composition comprising as an active ingredient a compound of formula (I) or a pharmaceutically acceptable salt thereof, and optionally a pharmaceutically acceptable carrier.

The present compounds of formula (I) can usually be administered in various dosage forms which include the preparations adapted for oral or parenteral administration. The oral preparations include tablets, hard and soft capsules, granules, powders, syrups and elixirs. The parenteral preparations include injections (intravenous, intramuscular, subcutaneous, intraperitoneal), drops and suppositories. These preparations can be prepared by conventional methods employing conventional additives such as excipients, binders, disintegrants, lubricants, flavorings, solubilizing aids, suspending agents, coating agents or the like. Route and dosage of administration for the compounds of the invention are not specifically limited and are appropriately chosen depending upon form of the preparations, age, sex and weight of the patient, severity of the disease and other factors. Daily dosage of the active ingredient for adult is 0.1 to 600 mg. No adverse toxicological effects are indicated at any of the above dosage range.

The invention is further illustrated by the following Examples.

Preparation Example 1

N,N'-bis(3,4-diethoxybenzyl)-N-solanesylethylenediamine

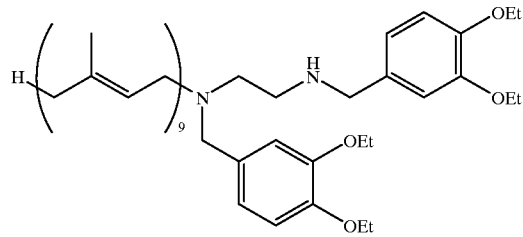

To a solution of N,N'-bis(3,4-diethoxybenzyl) ethylenediamine (16.7 g, 40 mmol) in tetrahydrofuran (100 ml) was added dropwise a solution of solanesylbromide (6.94 g, 10 mmol) in tetrahydrofuran (70 ml) at room temperature over a period of 2 hours with stirring. After the mixture was further stirred at room temperature for 3.5 hours, a saturated aqueous solution of potassium carbonate (100 ml) and ethyl acetate (100 ml) were added and the mixture was stirred at room temperature. The organic layer was concentrated, and to the residue was added hexane (200 ml) and acetonitrile (100 ml). The mixture was stirred at room temperature. Most of unreacted N,N'-bis(3,4-diethoxybenzyl)ethylenediamine were recovered as a acetonitrile layer. The hexane layer was concentrated and the residue was subjected to a silica gel column chromatography to give 6.75 g of N,N'-bis(3,4-diethoxybenzyl)-N-solanesylethylenediamine (yield 66%) as a brown oily product, which was converted to the dihydrochloride by conventional method.

Free base: $^1$H NMR (CDCl$_3$) δ 1.41 (t, J=6.8 Hz, 3H), 1.42 (t, J=6.8 Hz, 9H), 1.60 (s, 24H), 1.64 (s, 3H), 1.68 (s, 3H), 1.90–2.10 (m, 32H), 2.59 (t, J=5.8 Hz, 2H), 2.67 (t, J=5.8 Hz, 2H), 3.03 (d, J=6.4Hz, 2H), 3.46 (s, 2H), 3.62 (s, 2H), 4.03 (q, J=6.8 Hz, 2H), 4.06 (q, J=6.8 Hz, 2H), 5.08–5.13 (m, 8H), 5.28 (t, J=6.4 Hz, 1H), 6.75–6.84 (m, 6H).

Dihydrochloride: $^1$H NMR (CDCl$_3$) ( 1.42–1.48 (m, 12H), 1.60 (s, 27H), 1.67 (s, 3H), 1.90–2.20 (m, 32H), 3.04 (br, 1H), 3.20 (br, 1H), 3.82 (br, 2H), 4.02 (br, 2H), 4.07–4.19 (m, 10H), 5.05–5.15 (m, 8H), 5.43 (t, 1H), 6.82 (d, J=7.8 Hz, 1H), 6.92 (d, J=7.8 Hz, 1H), 6.83 (d, J=7.8 Hz, 1H), 6.93 (d, J=7.8 Hz, 1H), 10.43 (br, 1H), 10.59 (br, 1H), 11.76 (br, 1H).

Preparation Example 2

N,N'-bispiperonylbenzyl-N-solanesylethylenediamine

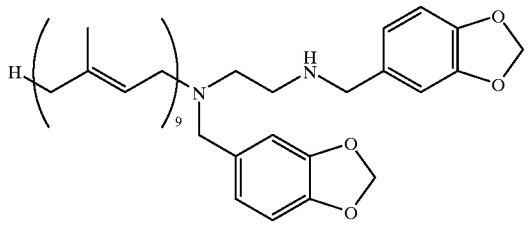

The title compound was prepared by a similar way as in Preparation Example 1, except for using N,N'-bispiperonylbenzylethylenediamine instead of N,N'-bis(3,4-diethoxybenzyl)ethylenediamine. The title compound was converted to the dihydrochloride by conventional method.

Free base: $^1$H NMR (CDCl$_3$) δ 1.59 (s, 3H), 1.60 (s, 24H), 1.68 (s, 3H), 1.90–2.10 (m, 32H), 2.57 (t, J=5.4 Hz, 2H), 2.65 (t, J=5.4 Hz, 2H), 3.02 (d, J=6.8 Hz, 2H), 3.43 (s, 2H), 3.60 (s, 2H), 5.05–5.15 (m, 8H), 5.26 (t, J=6.8 Hz, 1H), 5.93 (s, 4H), 6.68–6.80 (m, 6H).

Dihydrochloride: m.p. 141 ° C.; $^1$H NMR (CDCl$_3$) δ 1.60 (s, 24H), 1.68 (s, 3H), 1.70 (s, 3H), 1.90–2.20 (m, 32H), 3.15 (br, 1H), 3.29 (br, 1H), 3.72 (br, 2H), 3.87 (br, 2H), 4.03 (br, 2H), 4.18 (br, 2H), 5.05–5.15 (m, 8H), 5.48 (t, J=7.3 Hz, 1H), 5.96 (s, 2H), 6.00 (d, J=5.4 Hz, 2H), 6.79 (d, J=7.8 Hz, 1H), 6.81 (d, J=7.8 Hz, 1H), 7.04 (d, J=7.8 Hz, 1H), 7.11 (s, 1H), 7.16 (s, 1H), 10.50 (br, 1H), 10.59 (br, 1H), 11.79 (br, 1H).

Preparation Example 3

N,N'-bis(4-hydroxy-3-methoxybenzyl)-N-solanesylethylenediamine

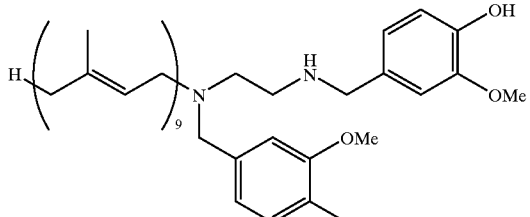

The title compound was prepared by a similar way as in Preparation Example 1, except for using N,N'-bis(4-hydroxy-3-methoxybenzyl)ethylenediamine instead of N,N'-bis(3,4-diethoxybenzyl)ethylenediamine. Yield 30%. The title compound was converted to the dihydrochloride by conventional method.

Free base: $^1$H NMR (CDCl$_3$) δ 1.60 (s, 27H), 1.68 (s, 3H), 1.92–2.13 (m, 32H), 2.62 (t, J=5.5 Hz, 2H), 2.70 (t, J=5.5 Hz, 2H), 3.07 (d, J=6.5 Hz, 2H ), 3.47 (s, 2H), 3.61 (s, 2H), 3.76 (s, 6H), 3.85 (s, 3H), 5.06–5.15 (m, 8H), 5.28 (t, J=6.5 Hz, 1H), 6.69–6.88 (m, 6H)

Preparation Example 4

N,N'-bis(3-chlorobenzyl)-N-solanesylethylenediamine

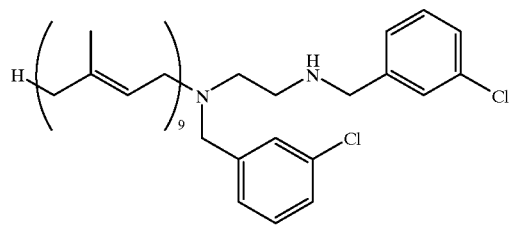

The title compound was prepared by a similar way as in Preparation Example 1, except for using N,N'-bis(3-chlorobenzyl)ethylenediamine instead of N,N'-bis(3,4-diethoxybenzyl)ethylenediamine. To a solution of N,N'-bis(3-chlorobenzyl)-N-solanesylethylenediamine (1.37 g, 1.489 mmol) in acetone was added fumaric acid (173 mg, 1.489 mmol) and the solution was allowed to stand overnight under cooling. The precipitated crystal was recovered by filtration to give 1.26 g of the fumarate of the title compound.

Free base: $^1$H NMR (CDCl$_3$) δ 1.58 (s, 3H), 1.60 (s, 24H), 1.68 (s, 3H), 1.90–2.15 (m, 30H), 2.55–2.70 (m, 4H), 3.03 (d, J=6.4 Hz, 2H), 3.50 (s, 2H), 3.66 (s, 2H), 5.05–5.15 (m, 8H), 5.26 (t, J=6.8 Hz, 1H), 7.10–7.30 (m, 8H).

Fumarate: m.p. 70–73° C.; $^1$H NMR (CDCl$_3$—CD$_3$OD) δ 1.57 (s, 3H), 1.60 (s, 24H), 1.68 (s, 3H), 1.90–2.20 (brm, 30H), 2.58–2.81 (m, 2H), 2.82–2.97 (m, 2H), 3.03–3.17 (m, 2H), 3.56 (brs, 2H), 3.93 (brs, 2H), 5.02–5.35 (m, 9H), 6.75 (brs, 2H), 7.10–7.42 (m, 8H).

Preparation Example 5

N,N'-bis(2,4-dimethoxybenzyl)-N-solanesylethylenediamine

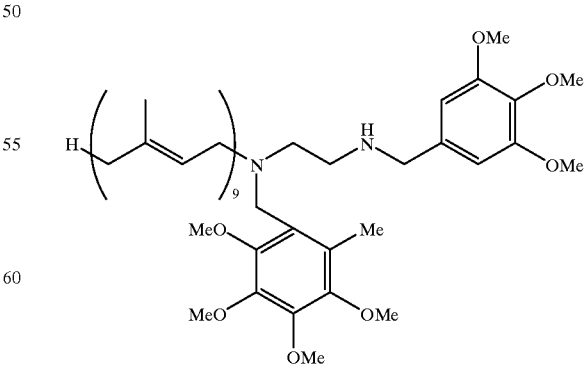

The title compound was prepared by a similar way as in Preparation Example 1, except for using N,N'-bis(2,4- dimethoxybenzyl)ethylenediamine, instead of N,N'-bis(3,4-diethoxybenzyl)ethylenediamine. The title compound was converted to the dihydrochloride by conventional method.

Free base: ¹H NMR (CDCl$_3$) δ 1.50–1.65 (m, 27H), 1.68 (s, 3H), 1.90–2.15 (m, 32H), 2.62 (m, 2H), 2.73 (m, 2H), 3.00 (d, J=6.8 Hz, 2H), 3.65–3.75 (m, 10H), 3.79 (s, 6H), 5.15–5.05 (m, 8H), 5.27 (t, J=6.8 Hz, 1H), 6.35–6.45 (m, 4H), 7.14 (d, J=8.8 Hz, 1H), 7.19 (d, J=7.8 Hz, 1H).

Dihydrochloride: ¹H NMR (CDCl$_3$) δ 1.45–1.80 (m, 30H), 1.85–2.20 (m, 32H), 2.32 (m, 2H), 3.17 (m, 2H), 3.55–3.75 (m, 2H), 3.81 (s, 3H), 3.83 (s, 6H), 3.86 (s, 3H), 4.05–4.35 (m, 4H), 5.00–5.15 (m, 8H), 5.52 (m, 1H), 6.40–6.55 (m, 4H), 7.36 (m, 1H), 7.42 (m, 1H), 9.88 (br, 1H), 10.40 (br, 1H), 11.45 (br, 1H).

Preparation Example 6

N,N'-bis(6-methyl-2,3,4,5-tetramethoxybenzyl)-N-solanesylethylenediamine

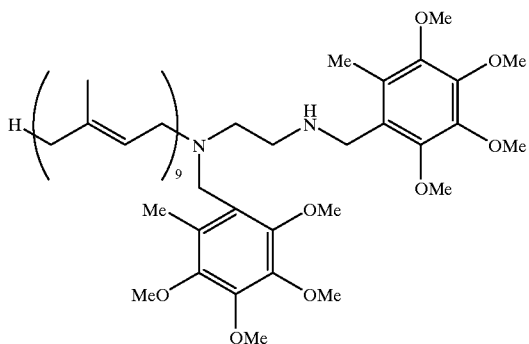

The title compound was prepared by a similar way as in Preparation Example 1, except for using N,N'-bis(6-methyl-2,3,4,5-tetramethoxybenzyl)ethylenediamine, instead of N,N'-bis(3,4-diethoxybenzyl)ethylenediamine. The title compound was converted to the dihydrochloride by conventional method.

Free base: ¹H NMR (CDCl$_3$) δ 1.60 (s, 27H), 1.68 (s, 3H), 1.90–2.10 (m, 32H), 2.20 (s, 3H), 2.22 (s, 3H), 2.52 (br, 2H), 2.67 (br, 2H), 2.96 (d, J=6.8 Hz, 2H), 3.64 (s, 2H), 3.70 (s, 2H), 3.72 (s, 3H), 3.76 (s, 3H), 3.78 (s, 3H), 3.81 (s, 3H), 3.86 (s, 3H), 3.89 (s, 3H), 3.90 (s, 6H), 5.05–5.15 (m, 8H), 5.31 (br, 1H).

Dihydrochloride: ¹H NMR (CDCl$_3$) δ 1.60 (s, 24H), 1.68 (s, 3H), 1.74 (s, 3H), 1.85–2.20 (m, 32H), 2.34 (s, 3H), 2.40 (s, 3H), 3.15 (br, 1H), 3.29 (br, 1H), 3.60–4.25 (m, 8H), 3.77 (s, 3H), 3.78 (s, 3H), 3.87 (s, 3H), 3.88 (s, 3H), 3.89 (s, 3H), 3.90 (s, 3H), 3.93 (s, 3H), 3.96 (s, 3H), 5.05–5.15 (m, 8H), 5.53 (br, 1H), 10.23 (br, 1H), 10.45 (br, 1H), 11.06 (br, 1H).

Preparation Example 7

N-(3,4-dimethoxybenzyl)-N'-(6-methyl-2,3,4,5-tetramethoxybenzyl)-N-solanesylethylenediamine

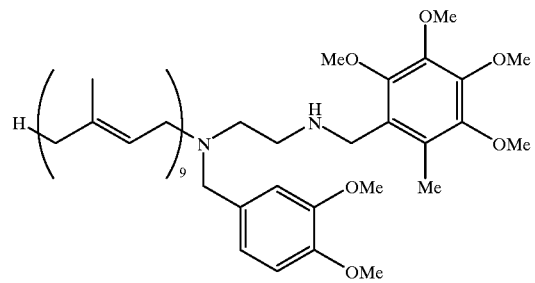

A mixture of N-(3,4-dimethoxybenzyl)-N-solanesylethylenediamine (5.0 g, 6.1 mmol), 6-methyl-2,3,4,5-tetramethoxybenzaldehyde (1.7 g, 7.0 mmol) and methanol (5 ml) was heated under reflux for one hour with stirring. After cooling, sodium borohydride (0.23 g, 6.1 mmol) was added at room temperature with stirring and the mixture was further stirred at room temperature for two hours. The solvent was concentrated under reduced pressure, and to the residue was added chloroform and 5% aqueous sodium hydroxide solution. The mixture was stirred at room temperature. The organic layer was washed with saturated saline, dried over magnesium sulfate and concentrated. A silica gel column chromatography of the residue gave 5.41 g (85%) of the title compound as a yellow oily product. The title compound was converted to the dihydrochloride by conventional method.

Free base: ¹H NMR (CDCl$_3$) δ 1.55 (s, 3H), 1.60 (s, 24H), 1.68 (s, 3H), 1.90–2.10 (m, 32H), 2.22 (s, 3H), 2.60 (t, J=5.9 Hz, 2H), 2.73 (t, J=5.8 Hz, 2H), 3.01 (d, J=6.8 Hz, 2H), 3.49 (s, 2H), 3.70 (s, 2H), 3.76 (s, 3H), 3.82 (s, 6H), 3.85 (s, 3H), 3.86 (s, 3H), 3.89 (s, 3H), 5.05–5.15 (m, 8H), 5.28 (t, J=6.8 Hz, 1H), 6.62–6.79 (m, 2H), 6.86 (s, 1H).

Dihydrochloride: ¹H NMR (CDCl$_3$) δ 1.53 (s, 3H), 1.60 (s, 21H), 1.62 (s, 3H), 1.68 (s, 3H), 1.90–2.20 (m, 32H), 2.38 (s, 3H), 3.21 (br, 2H), 3.33 (br, 2H), 3.69 (br, 2H), 3.77 (s, 3H), 3.87 (s, 3H), 3.88 (s, 6H), 3.94 (s, 6H), 4.09–4.25 (m, 4H), 5.05–5.15 (m, 8H), 5.40–5.50 (m, 1H), 6.80–6.85 (m, 1H), 6.93–6.98 (m, 1H), 7.45 (s, 1H), 10.12 (br, 2H), 11.88 (br, 1H).

Preparation Example 8

N-(3,4-dimethoxybenzyl)-N'-(2-hydroxy-3-methoxybenzyl)-N-solanesylethylenediamine

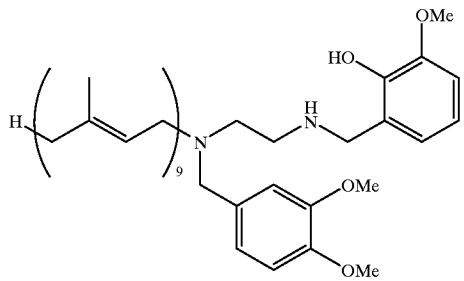

The title compound was prepared by a similar way as in Preparation Example 7, except that 2-hydroxy-3- methoxybenzaldehyde was used instead of 6-methyl-2,3,4,5-tetramethoxybenzaldehyde. Yield 76%. The title compound was converted to the dihydrochloride by conventional method.

Free base: $^1$H NMR (CDCl$_3$) δ 1.60 (s, 27H), 1.68 (s, 3H), 1.90–2.10 (m, 32H), 2.55–2.70 (m, 4H), 3.07 (d, J=6.4 Hz, 2H), 3.50 (s, 2H), 3.81 (s, 2H), 3.82 (s, 3H), 3.86 (s, 3H), 3.87 (s, 3H), 5.05–5.15 (m, 8H), 5.28 (t, J=6.4 Hz, 1H), 6.52 (d, J=7.3 Hz, 1H), 6.68–6.86 (m, 5H).

Dihydrochloride (brown oily): $^1$H NMR (CDCl$_3$) δ 1.60 (s, 27H), 1.67 (s, 3H), 1.90–2.20 (m, 32H), 3.23 (br, 2H), 3.70 (br, 2H), 3.85 (s, 3H), 3.87 (s, 3H), 3.93 (s, 3H), 3.89 (br, 2H), 4.19 (s, 4H), 5.05–5.15 (m, 8H), 5.45 (t, J=7.4 Hz, 1H), 6.81–7.00 (m, 4H), 7.13 (m, 1H), 7.43 (s, 1H), 10.4 (br, 2H), 11.7 (br, 1H).

Preparation Example 9

N'-(3,4-dimethoxybenzyl)-N-(6-methyl-2,3,4,5-tetramethoxybenzyl)-N-solanesylethylenediamine

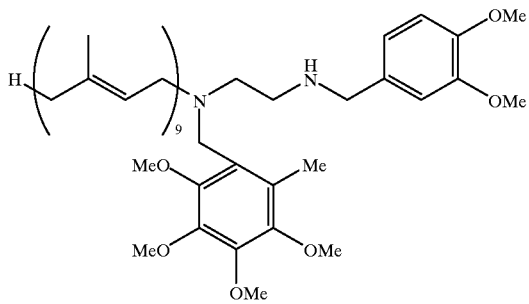

The title compound was prepared by a similar way as in Preparation Example 7, except that N-(6-methyl-2,3,4,5-tetramethoxybenzyl)-N-solanesylethylenediamine was used instead of N-(3,4-dimethoxybenzyl)-N-solanesylethylenediamine and veratraldehyde was used instead of 6-methyl-2,3,4,5-tetramethoxybenzaldehyde. Yield 85%. The title compound was converted to the dihydrochloride by conventional method.

Free base: $^1$H NMR (CDCl$_3$) δ 1.60 (s, 27H), 1.68 (s, 3H), 1.90–2.10 (m, 32H), 2.24 (s, 3H), 2.55 (br, 2H), 2.65 (br, 2H), 3.00 (d, J=6.3 Hz, 2H), 3.51 (s, 2H), 3.55 (s, 2H), 3.73 (s, 3H), 3.74 (s, 3H), 3.86 (s, 3H), 3.87 (s, 6H), 3.90 (s, 3H), 5.05–5.15 (m, 8H), 5.30 (t, J=6.3 Hz, 1H), 6.74–6.89 (m, 3H).

Dihydrochloride (brown oily): $^1$H NMR (CDCl$_3$) δ 1.60 (s, 24H), 1.68 (s, 3H), 1.74 (s, 3H), 1.90–2.20 (m, 32H), 2.34 (s, 3H), 3.01 (br, 1H), 3.21 (br, 1H), 3.77 (s, 3H), 3.85 (s, 3H), 3.87 (s, 3H), 3.90 (s, 3H), 3.94 (s, 3H), 3.95 (s, 3H), 3.66–4.27 (m, 8H), 5.05–5.15 (m, 8H), 5.50–5.60 (m, 1H), 6.80 (d, J=8.3 Hz, 1H), 7.01 (d, J=8.3 Hz, 1H), 7.41 (s, 1H), 10.52 (br, 1H), 10.64 (br, 1H), 10.86 (br, 1H).

Preparation Example 10

N-(6-methyl-2,3,4,5-tetramethoxybenzyl)-N-solanesyl-N'-(3,4,5-trimethoxybenzyl)ethylenediamine

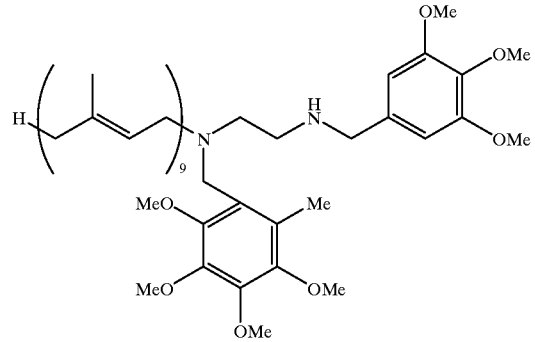

The title compound was prepared as a yellow oily product, by a similar way as in Preparation Example 7, in a solvent of methanol/chloroform (3/1, (v/v)), except that N-(6-methyl-2,3,4,5-tetramethoxybenzyl)-N-solanesylethylenediamine was used instead of N-(3,4-dimethoxybenzyl)-N-solanesylethylenediamine, and 3,4,5-trimethoxybenzaldehyde was used instead of 6-methyl-2,3,4,5-tetramethoxybenzaldehyde. Yield 83%. The title compound was converted to the dihydrochloride by conventional method.

Free base: $^1$H NMR (CDCl$_3$) δ 1.60 (s, 27H), 1.68 (s, 3H), 1.90–2.10 (m, 32H), 2.25 (s, 3H), 2.56 (t, 2H), 2.65 (t, 2H), 3.01 (d, J=6.8 Hz, 2H), 3.52 (s, 2H), 3.53 (s, 2H), 3.72 (s, 3H), 3.80 (s, 3H), 3.82 (s, 3H), 3.85 (s, 6H), 3.87 (s, 3H), 3.89 (s, 3H), 5.05–5.15 (m, 8H), 5.31 (t, 1H), 6.50 (s, 2H).

Dihydrochloride (brown oily): $^1$H NMR (CDCl$_3$) δ 1.59 (s, 24H), 1.67 (s, 3H), 1.74 (s, 3H), 1.90–2.20 (m, 32H), 2.34 (s, 3H), 3.07 (br, 1H), 3.24 (br, 1H), 3.78 (s, 3H), 3.83 (s, 3H), 3.85 (s, 3H), 3.88 (s, 3H), 3.90 (s, 3H), 3.94 (s, 3H), 3.72–4.29 (m, 8H), 5.05–5.15 (m, 8H), 5.57 (t, J=6.8 Hz, 1H), 6.94 (s, 2H), 10.54 (br, 1H), 10.64 (br, 1H), 10.83 (br, 1H).

Preparation Example 11

N'-(2,4-difluorobenzyl)-N-(3,4-dimethoxybenzyl)-N-solanesylethylenediamine

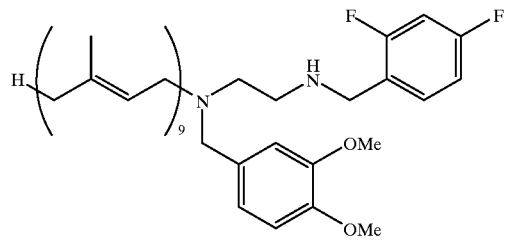

The title compound was prepared as a yellow oily product, by a similar way as in Preparation Example 7, except that 2,4-difluorobenzaldehyde was used instead of 6-methyl-2,3,4,5-tetramethoxybenzaldehyde. Yield 38%. The title compound was converted to the dihydrochloride by conventional method.

Free base: $^1$H NMR (CDCl$_3$) δ 1.60 (s, 24H), 1.62 (s, 3H), 1.68 (s, 3H), 1.90–2.10 (m, 32H), 2.59 (t, J=5.6 Hz, 2H), 2.66 (t, J=5.6 Hz, 2H), 3.03 (d, J=6.4 Hz, 2H), 3.47 (s, 2H), 3.71 (s, 2H), 3.82 (s, 3H), 3.86 (s, 3H), 5.05–5.15 (m, 8H), 5.27 (t, J=6.4 Hz, 1H), 6.73–6.88 (m, 5H), 7.24 (m, 1H).

Dihydrochloride (yellow oily): $^1$H NMR (CDCl$_3$) δ 1.60 (s, 24H), 1.68 (s, 3H), 1.70 (s, 3H), 1.90–2.20 (m, 32H), 3.04–4.23 (m, 10H), 3.89 (s, 3H), 3.92 (s, 3H), 5.05–5.15 (m, 8H), 5.48 (t, 1H), 6.84 (m, 2H), 6.97 (m, 2H), 7.40 (s, 1H), 7.82 (m, 1H), 10.60 (br, 1H), 10.80 (br, 1H), 11.57 (br, 1H).

Preparation Example 12

N-(3,4-dimethoxybenzyl)-N-solanesyl-N'-(3,4,5-trimethoxybenzyl)ethylenediamine

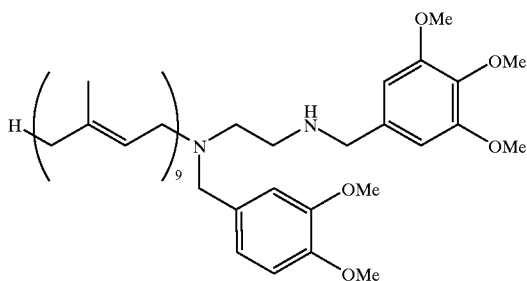

The title compound was prepared by a similar way as in Preparation Example 7, in a solvent of methanol/chloroform (3/1, (v/v)), except that 3,4,5-trimethoxybenzaldehyde was used instead of 6-methyl-2,3,4,5-tetramethoxybenzaldehyde. Yield 78%. The title compound was converted to the dihydrochloride by conventional method.

Free base: $^1$H NMR (CDCl$_3$) δ 1.60 (s, 24H), 1.65 (s, 3H), 1.68 (s, 3H), 1.90–2.15 (m, 32H), 2.61 (t, J=5.9 Hz, 2H), 2.70 (t, J=5.9 Hz, 2H), 3.07 (d, J=6.4 Hz, 2H), 3.50 (s, 2H), 3.64 (s, 2H), 3.80 (s, 3H), 3.82 (s, 3H), 3.84 (s, 6H), 3.85 (s, 3H), 5.05–5.15 (m, 8H), 5.30 (t, J=6.4 Hz, 1H), 6.53 (s, 2H), 6.76–6.82 (m, 5H), 6.24 (s, 1H).

Dihydrochloride (yellow oily): $^1$H NMR (CDCl$_3$) δ 1.60 (s, 24H), 1.68 (s, 6H), 1.90–2.20 (m, 32H), 3.15 (br, 1H), 3.30 (br, 1H), 3.66–4.20 (m, 8H), 3.84 (s, 3H), 3.88 (s, 3H), 3.90 (s, 6H), 3.95 (s, 3H), 5.05–5.15 (m, 8H), 5.40–5.50 (m, 1H), 6.84 (d, J=8.3 Hz, 1H), 6.94 (s, 2H), 6.97 (d, J=8.3 Hz, 1H), 10.55 (br, 2H), 11.73 (br, 1H).

Preparation Example 13

N'-(3,4-difluorobenzyl)-N-(3,4-dimethoxybenzyl)-N-solanesylethylenediamine

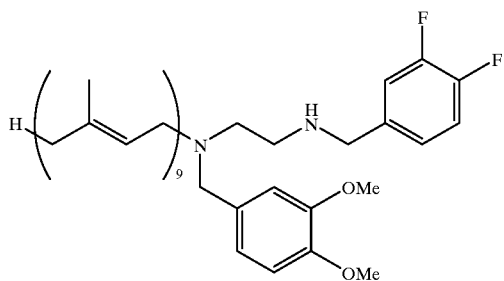

The title compound was prepared by a similar way as in preparation Example 7, in a solvent of methanol/chloroform (3/1, (v/v)), except that 3,4-difluorobenzaldehyde was used instead of 6-methyl-2,3,4,5-tetramethoxybenzaldehyde. Yield 82%. The title compound was converted to the dihydrochloride by conventional method.

Free base: $^1$H NMR (CDCl$_3$) δ 1.60 (s, 27H), 1.68 (s, 3H), 1.90–2.17 (m, 32H), 2.59 (t, J=5.4 Hz, 2H), 2.64 (t, J =5.4 Hz, 2H), 3.06 (d, J=6.8 Hz, 2H), 3.49 (s, 2H), 3.61 (s, 2H), 3.81 (s, 3H), 3.86 (s, 3H), 5.05–5.15 (m, 8H), 5.29 (t, J=6.8 Hz, 1H), 6.77–7.14 (m, 6H).

Dihydrochloride (yellow oily): $^1$H NMR (CDCl$_3$) δ 1.60 (s, 24H), 1.68 (s, 3H), 1.71 (s, 3H), 1.90–2.20 (m, 32H), 3.07 (br, 1H), 3.29 (br, 1H), 3.89 (s, 3H), 3.95 (s, 3H), 3.69–4.17 (m, 8H), 5.05–5.15 (m, 8H), 5.46 (t, 1H), 6.84–7.56 (m, 6H), 10.65 (br, 1H), 10.80 (br, 1H), 11.68 (br, 1H).

Preparation Example 14

N-(3,4-dimethoxybenzyl)-N-solanesyl-N'-(2,4,6-trimethoxybenzyl)ethylenediamine

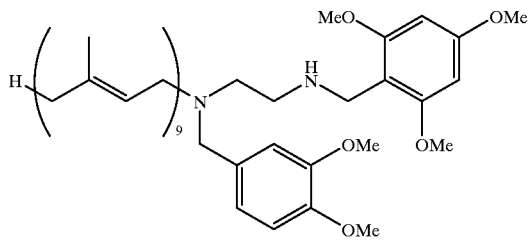

The title compound was prepared by a similar way as in Preparation Example 7, in a solvent of methanol/chloroform (3/1, (v/v)), except that 2,4,6-trimethoxybenzaldehyde was used instead of 6-methyl-2,3,4,5-tetramethoxybenzaldehyde. Yield 98%. The title compound was converted to the dihydrochloride by conventional method.

Free base: $^1$H NMR (CDCl$_3$) δ 1.54 (s, 3H), 1.60 (s, 24H), 1.68 (s, 3H), 1.90–2.10 (m, 32H), 2.57–2.65 (m, 2H), 2.65–2.73 (m, 2H), 2.98 (d, J=6.8 Hz, 2H), 3.48 (s, 2H), 3.76 (s, 6H), 3.79 (s, 2H), 3.79 (s, 3H), 3.82 (s, 3H), 3.85 (s, 3H), 5.05–5.15 (m, 8H), 5.23 (t, J=6.8 Hz, 1H), 6.10 (s, 2H), 6.77 (s, 2H), 6.85 (s, 1H).

Dihydrochloride (yellow oily): $^1$H NMR (CDCl$_3$) δ 1.60 (s, 24H), 1.68 (s, 6H), 1.90–2.20 (m, 32H), 2.93 (br, 1H), 3.14 (br, 1H), 3.67 (br, 2H), 3.82 (s, 6H), 3.83 (s, 3H), 3.88 (s, 6H), 3.90 (br, 2H), 4.10–4.25 (m, 4H), 5.05– 4.15 (m, 8H), 5.46 (br, 1H), 6.08 (d, J=8.3 Hz, 1H), 6.90 (d, J=8.3 Hz, 1H), 7.42 (s, 1H), 9.75 (br, 1H), 9.95 (br, 1H), 12.21 (br, 1H).

Preparation Example 15

N-(3,4-difluorobenzyl)-N-solanesyl-N'-(2,4,6-trimethoxybenzyl)ethylenediamine

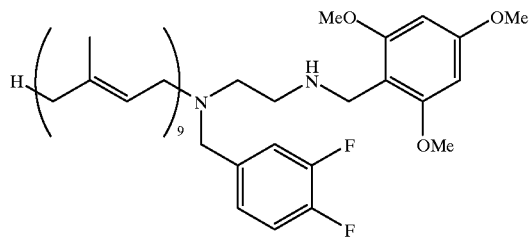

The title compound was prepared as a yellow oily product, by a similar way as in Preparation Example 7, in a solvent of methanol/chloroform (3/1, (v/v)), except that N-(3,4-difluorobenzyl)-N-solanesylethylenediamine was used instead of N-(3,4-dimethoxybenzyl)-N-solanesylethylenediamine, and 2,4,6-trimethoxybenzaldehyde was used instead of 6-methyl-2,3,4,5-tetramethoxybenzaldehyde. Yield 86%. The title compound was converted to the dihydrochloride by conventional method.

Free base: $^1$H NMR(CDCl$_3$)δ1.51 (s, 3H), 1.60 (s, 24H), 1.68 (s, 3H), 1.90–2.10 (m, 32H), 2.55–2.67 (m, 4H), 2.94 (d, J=6.4 Hz, 2H), 3.43 (s, 2H), 3.76 (s, 2H), 3.78 (s, 6H), 3.80 (s, 3H), 5.05–5.15 (m, 8H), 5.22 (t, J=6.4 Hz, 1H), 6.11 (s, 2H), 6.90–7.15 (m, 3H).

Dihydrochloride (brown oily): $^1$H NMR (CDCl$_3$) δ 1.60 (s, 24H), 1.66 (s, 3H), 1.68 (s, 3H), 1.90–2.20 (m, 32H), 2.57 (br, 2H), 3.01 (br, 1H), 3.20 (br, 1H), 3.68 (br, 2H), 4.07–4.40 (m, 4H), 5.03–5.15 (m, 8H), 5.40–5.50 (m, 1H), 6.10 (s, 2H), 7.10–7.20 (m, 1H), 7.43–7.50 (br, 1H), 7.50–7.60 (m, 1H), 9.70 (br, 1H), 9.82 (br, 1H), 12.30 (br, 1H).

Preparation Example 16

N,N'-bis(3,4-difluorobenzyl)-N-solanesylethylenediamine

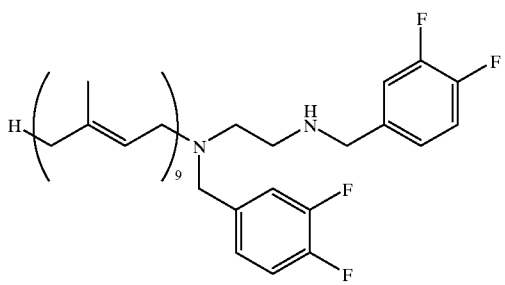

The title compound was prepared as a yellow oily product by a similar way as in Preparation Example 7, in a solvent of methanol/chloroform (3/1, (v/v)), except that N-(3,4-difluorobenzyl)-N-solanesylethylenediamine was used instead of N-(3,4-dimethoxybenzyl)-N-solanesylethylenediamine, and 3,4-difluorobenzaldehyde was used instead of 6-methyl-2,3,4,5-tetramethoxybenzaldehyde. Yield 90%. The title compound was converted to the dihydrochloride by conventional method.

Free base: $^1$H NMR (CDCl$_3$) δ 1.60 (s, 27H), 1.68 (s, 2H), 1.90–2.10 (m, 32H), 2.57–2.63 (m, 4H), 3.02 (d, J=6.8 Hz, 2H), 3.48 (s, 2H), 3.65 (s, 2H), 5.05–5.15 (m, 8H), 5.24 (t, J=6.8 Hz, 1H), 6.97–7.14 (m, 6H).

Dihydrochloride (white amorphous solid): $^1$H NMR (CDCl$_3$) δ 1.60 (s, 24H), 1.68 (s, 3H), 1.69 (s, 3H), 1.90–2.25 (m, 32H), 3.33–4.38 (m, 10H), 5.05–5.15 (m, 8H), 5.40–5.50 (m, 1H), 7.15–7.25 (m, 2H), 7.44 (br, 2H), 7.55–7.65 (m, 2H), 10.70 (br, 2H), 11.91 (br, 1H).

Preparation Example 17

N'-(3,4-dimethoxybenzyl)-N-solanesyl-N-(2,4,6-trimethoxybenzyl)ethylenediamine

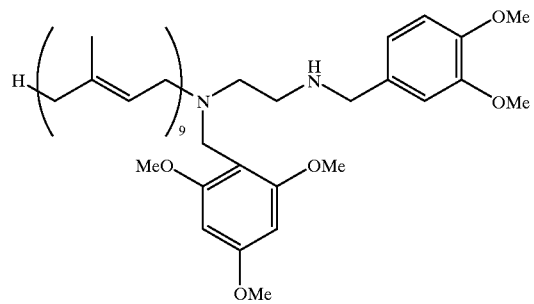

The title compound was prepared as a yellow oily product by a similar way as in Preparation Example 7, in a solvent of methanol/chloroform (3/1, (v/v)), except that N-solanesyl-N-(2,4,6-trimethoxybenzyl)ethylenediamine was used instead of N-(3,4-dimethoxybenzyl)-N-solanesylethylenediamine, and veratraldehyde was used instead of 6-methyl-2,3,4,5-tetramethoxybenzaldehyde. Yield 84%. The title compound was converted to the dihydrochloride by conventional method.

Free base: $^1$H NMR (CDCl$_3$) δ 1.60 (s, 27H), 1.68 (s, 3H), 1.90–2.10 (m, 32H), 2.61 (br, 2H), 2.79 (br, 2H), 3.03 (d, J=6.8 Hz, 2H), 3.55 (s, 2H), 3.70 (s, 2H), 3.70 (s, 6H), 3.79 (s, 3H), 3.85 (s, 3H), 3.86 (s, 3H), 5.05–5.15 (m, 8H), 5.32 (t, J=6.8 Hz, 1H), 6.09 (s, 2H), 6.75–6.85 (m, 2H), 6.97 (br, 1H).

Dihydrochloride (yellow oily): $^1$H NMR (CDCl$_3$) δ 1.60 (s, 24H), 1.68 (s, 3H), 1.71 (s, 3H), 1.90–2.20 (m, 32H), 3.15 (br, 2H), 3.52–3.77 (m, 4H), 3.84 (s, 6H), 3.87 (s, 3H), 3.96 (s, 3H), 3.98–4.35 (m, 4H), 5.05–5.15 (m, 8H), 5.52 (t, 1H), 6.11 (s, 2H), 6.82 (d, J=8.3 Hz, 1H), 7.04 (d, J=8.3 Hz, 1H), 7.45 (s, 1H), 10.42 (br, 1H), 10.64 (br, 1H), 10.84 (br, 1H).

Preparation Example 18

N,N'-bis(2,4,6-trimethoxybenzyl)-N-solanesylethylenediamine

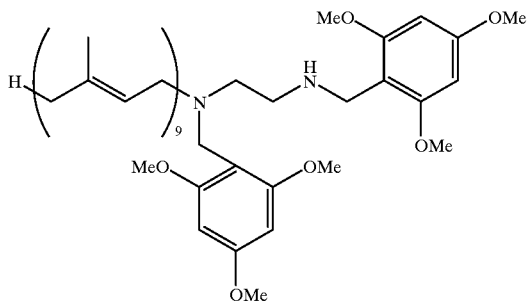

The title compound was prepared as a yellow oily product by a similar way as in Preparation Example 7, in a solvent of methanol/chloroform (3/1, (v/v)), except that N-solanesyl-N-(2,4,6-trimethoxybenzyl)ethylenediamine was used instead of N-(3,4-dimethoxybenzyl)-N-solanesylethylenediamine, and 2,4,6-trimethoxybenzaldehyde was used instead of 6-methyl-2,3,4,5-tetramethoxybenzaldehyde. Yield 68%. The title compound was converted to the dihydrochloride by conventional method.

Free base: $^1$H NMR (CDCl$_3$) δ 1.60 (s, 27H), 1.68 (s, 3H), 1.90–2.10 (m, 32H), 2.58 (br, 2H), 2.74 (br, 2H), 3.00 (br, 2H), 3.56 (s, 2H), 3.74 (s, 2H), 3.74 (s, 6H), 3.75 (s, 6H), 3.79 (s, 3H), 3.80 (s, 3H), 5.05–5.15 (m, 8H), 5.33 (br, 1H), 6.09 (s, 4H).

Dihydrochloride (yellow oily): $^1$H NMR (CDCl$_3$) δ 1.60 (s, 24H), 1.68 (s, 3H), 1.71 (s, 3H), 1.90–2.20 (m, 32H), 2.29 (br, 2H), 3.13 (br, 2H), 3.53 (br, 2H), 3.80 (s, 6H), 3.82 (s, 3H), 3.84 (s, 9H), 4.02–4.21 (m, 4H), 5.05–5.15 (m, 8H), 5.51 (t, J=6.8 Hz, 1H), 6.08 (s, 2H), 6.09 (s, 2H), 9.56 (br, 1H), 10.23 (br, 1H), 10.97 (br, 1H).

Pharmaceutical Example 1

Hard Capsules

A mixture of 25 g of N,N'-bis(6-methyl-2,3,4,5-tetramethoxybenzyl)-N-solanesylethylenediamine (the compound of Preparation Example 6) and 7.5 g of polyoxyethylene castor oil in methanol was mixed with 25 g of silicic anhydride. After evaporation of methanol, the mixture was further mixed with 5 g of calcium carboxymethylcellulose, 5 g of corn starch, 7.5 g of hydroxypropylcellulose and 20 g of microcrystalline cellulose, and further 30 ml of water. The mixture was kneaded to give a granular mass. The mass was pelletized by means of a pelletizer equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 200 mg per capsule.

Pharmaceutical Example 2

Soft Capsules

A homogeneous solution was prepared by mixing 30 g of N,N'-bis(6-methyl-2,3,4,5-tetramethoxybenzyl)-N-solanesylethylenediamine (the compound of Preparation Example 6) with 130 g of polyethylene glycol (Macrogol 400). Separately, a gelatin solution was prepared which contained 93 g of gelatin, 19 g of glycerol, 10 g of D-sorbitol, 0.4 g of ethyl p-hydroxybenzoate, 0.2 g of propyl p-hydroxybenzoate and 0.4 g of titanium oxide. The gelatin solution was used as a capsule film forming agent. The previously obtained solution, together with the capsule film forming agent, was treated with a manual type flat punching machine to obtain capsules, each having the contents of 190 mg.

Pharmaceutical Example 3

Soft Capsules

A homogeneous solution was prepared by mixing 40 g of N,N'-bis(6-methyl-2,3,4,5-tetramethoxybenzyl)-N-solanesylethylenediamine (the compound of Preparation Example 6) with 120 g of polyethylene glycol (Macrogol 400). Separately, a gelatin solution was prepared which contained 90 g of gelatin, 16 g of glycerol, 18 g of D-sorbitol, 0.35 g of ethyl p-hydroxybenzoate, 0.2 g of propyl p-hydroxybenzoate and 0.3 g of titanium oxide. The gelatin solution was used as a capsule film forming agent. The previously obtained solution, together with the capsule film forming agent, was treated with a manual type flat punching machine to obtain capsules, each having the contents of 180 mg.

Pharmaceutical Example 4

Injections 5 g of N,N'-bis(6-methyl-2,3,4,5-tetramethoxybenzyl)-N-solanesylethylenediamine dihydrochloride (the compound of Preparation Example 6), an appropriate amount of peanut oil and 1 g of benzyl alcohol were mixed, and further peanut oil was added to the mixture to make up a total volume of 100 ml. This solution was dispensed in an amount of 1 ml under asepsis operation into an ampule which was then sealed.

Pharmaceutical Example 5

Injections 9 g of N,N'-bis(6-methyl-2,3,4,5-tetramethoxybenzyl)-N-solanesylethylenediamine dihydrochloride (the compound of Preparation Example 6), 5.0 g of hydrogenated castor oil polyoxyethylene (60 mols) ether ("Nikkol HCO 60" available from Nikko Chemical Co., Ltd.), 20 g of propylene glycol, 10 g of glycerol and 5.0 g of ethanol were mixed. To the mixture, 100 ml of distilled water were added and stirred. Under asepsis operation, this solution was dispensed in an amount of 2 ml into an ampule which was then sealed.

The pharmacological activities of the present compounds as multidrug resistance inhibitors are demonstrated by the following Examples.

Example 1

Colony Formation Assay for Adriamycin Resistant Cells (MCF 7/ADM) Derived from Human Breast Cancer A culture solution of adriamycin resistant cells (MCF 7/ADM) derived from human breast cancer, suspended in MEM (minimal essential medium, available from Nissui Seiyaku) containing 10% fetal calf serum, glutamine (2 μg/ml) and kanamycin (50 μg/ml), was prepared so as to give a concentration of 750 cells/ml. The solution was dispensed into a 12 well-microplate so as to give 1500 cells per well. The cells were incubated at 37° C. for 24 hours in 5% CO$_2$. A 0.50 mmol solution of each test compound in dimethyl sulfoxide was added cumulatively, and the cells were incubated at 37° C. for a week in 5% CO$_2$. After colonies were stained with 0.1% methylene blue in methanol for 30 minutes and dried, the number of colonies were counted by a microscope. The concentration of the compound required to inhibit 30% colony formation of cells, expressed by $IC_{30}$, was calculated from the counted number of colonies. The results are shown in the following Table 1.

TABLE 1

Colony formation assay

| Test compound | $IC_{30}$ ($\mu M$) |
|---|---|
| Compound of Preparation Example 4 (fumarate) | 50 |
| Compound of Preparation Example 6 (dihydrochloride) | 50 |
| Compound of formula (IV) (dihydrochloride) | 5 |

The above results indicate that compounds of the present invention has clearly lower cytotoxicity, as compared with a compound of formula (IV).

Example 2
Combined Effect of the Present Compounds and Adriamycin on Adriamycin Non-resistant Cells (MCF 7/WT) Derived from Human Breast Cancer A culture solution of adriamycin non-resistant cells (MCF 7/WT) derived from human breast cancer in MEM (minimal essential medium, available from Nissui Seiyaku) containing 10% fetal calf serum, glutamine (2 $\mu g/ml$) and kanamycin (50 $\mu g/ml$) was dispensed into a 12-well microplate so as to give 1000 cells per well. The cells were incubated at 37° C. for 24 hours in 5% $CO_2$. Adriamycin was cumulatively added to the culture solution at a range of 0–50 ng/mg, and a solution of each test compound in dimethyl sulfoxide was further added such that a final concentration becomes the $IC_{30}$ obtained in Example 1. The cells were incubated at 37° C. for a week in 5% $CO_2$. As the control, adriamycin alone was added to the culture solution as described above and the cells were incubated for a week in the same manner. After colonies were stained with 0.1% methylene blue in methanol for 30 minutes and dried, the number of colonies was counted by a microscope. The concentration of the compound required to inhibit 50% colony formation of cells, expressed by $IC_{50}$, was calculated from the counted number of colonies. Further, the potentiation activity (which is the relative value based on $IC_{50}$ value of the control, adriamycin) was determined.

The results are shown in the following Table 2.

TABLE 2

Combined effect of test compound and adriamycin (ADM) on MCF7/WT

| Test compound | Combined concentration ($\mu M$) | ADM ng/ml ($IC_{50}$) | Potentiation activity |
|---|---|---|---|
| Compound of Preparation Example 5 (dihydrochloride) | 2 | 7.2 | 0.72 |
| Compound of Preparation Example 6 (dihydrochloride) | 50 | 6.6 | 0.66 |
| Control (ADM) | — | 10 | 1.0 |

The above results indicate that the compounds of the present invention enhance anti-cancer activity of adriamycin in ADM non-resistant cells derived from human breast cancer.

Example 3
Combined Effect of the Present Compounds and Adriamycin on Adriamycin Resistant Cells (MCF 7/ADM) Derived from Human Breast Cancer A culture solution of adriamycin resistant cells (MCF 7/ADM) derived from human breast cancer in MEM (minimal essential medium, available from Nissui Seiyaku) containing 10% fetal calf serum, glutamine (2 $\mu g/ml$) and kanamycin (50 $\mu g/ml$), was dispensed into a 12 well-microplate so as to give 1500 cells per well. The cells were incubated at 37° C. for 24 hours in 5% $CO_2$. Adriamycin was cumulatively added to the culture solution at a range of 0–5000 ng/ml, and a solution of each test compound in dimethyl sulfoxide was further added such that a final concentration becomes the $IC_{30}$ value obtained in Example 1. The cells were incubated at 37° C. for a week in 5% $CO_2$. As the control, adriamycin alone was added to the culture solution as described above, and the cells were incubated for a week in the same way. After colonies were stained with 0.1% methylene blue in methanol for 30 minutes and dried, the number of colonies was counted by a microscope. The concentration of the compound required to inhibit 50% colony formation of cells, expressed by $IC_{50}$, was calculated, and the potentiation activity (which is the relative value based on $IC_{50}$ value of the control, adriamycin in Example 2) was calculated from the counted number of colonies. The results are shown in the following Table 3.

TABLE 3

Combined effect of test compound and adriamycin on MCF 7/ADM

| Test compound | Combined concentration ($\mu M$) | ADM ng/ml ($IC_{50}$) | Potentiation activity |
|---|---|---|---|
| Compound of Preparation Example 5 (dihydrochloride) | 2 | 560 | 56 |
| Compound of Preparation Example 6 (dihydrochloride) | 50 | 240 | 24 |
| Control | — | 1250 | 125 |
| Control (Example 2) | — | 10 | 1 |

The above results indicate that the compounds of the present invention have an activity overcoming multidrug resistance in adriamycin resistant cells derived from human breast cancer.

As evidenced by the above pharmacological tests, the compounds of formula (I) and its salts according to the invention have low cytotoxicity, and enhance an activity of anti-cancer agents in non-resistant cancer cells, and also have an activity overcoming resistance in multidrug resistant cancer cells.

Accordingly, the present compounds of formula (I) and its salts are useful as multidrug resistance inhibitors and anti-cancer activity potentiators.

What is claimed is:

1. A method for reducing multidrug resistance in cancer therapy or enhancing the activity of an anti-cancer agent, comprising: administering to a patient in need thereof an effective amount of a compound of formula (I) or a pharmaceutically acceptable salt thereof:

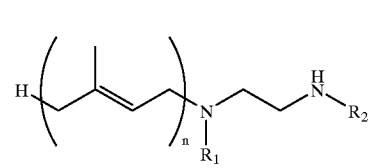

(I)

wherein
n is an integer of 5 to 12,
$R_1$ and $R_2$ are each independently benzyl, of which a phenyl ring may be substituted by 1 to 5 substituents selected from hydroxy, $(C_1-C_4)$alkyl, $(C_1-C_4)$alkoxy and halogen, and/or by methylenedioxy, with the proviso that $R_1$ and $R_2$ are simultaneously not a compound of formula (II):

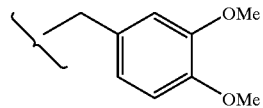
(II)

2. The method of claim 1, wherein the anti-cancer agent is used for the treatment of a cancer selected from the group consisting of brain tumor, kidney cancer, adrenal cancer, large intestine cancer, small intestine cancer, intestinum colon cancer, lung cancer, liver cancer, pancreas cancer and leukemia.

3. The method of claim 1, wherein the anti-cancer agent is taxol.

* * * * *